United States Patent
Hambüchen et al.

(10) Patent No.: US 7,305,062 B2
(45) Date of Patent: Dec. 4, 2007

(54) X-RAY SYSTEM HAVING A FIRST AND A SECOND X-RAY ARRAY

(75) Inventors: Klaus Hambüchen, Hemhofen (DE); Klaus Klingenbeck-Regn, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/314,838

(22) Filed: Dec. 21, 2005

(65) Prior Publication Data

US 2006/0165213 A1 Jul. 27, 2006

(30) Foreign Application Priority Data

Dec. 22, 2004 (DE) .................. 10 2004 061 933

(51) Int. Cl.
*A61B 6/03* (2006.01)
(52) U.S. Cl. ............................. 378/9; 378/4
(58) Field of Classification Search .......... 378/4–20, 378/55, 197–198, 65
See application file for complete search history.

(56) References Cited

U.S. PATENT DOCUMENTS

| 6,470,066 | B2* | 10/2002 | Takagi et al. ............ 378/8 |
| 7,016,455 | B2* | 3/2006 | Bruder et al. ............ 378/9 |
| 2003/0076920 | A1 | 4/2003 | Shinno et al. | |

FOREIGN PATENT DOCUMENTS

DE 103 02 565 A1 8/2004

\* cited by examiner

*Primary Examiner*—Hoon Song

(57) ABSTRACT

An X-ray system has two X-ray arrays each having an X-ray source and an X-ray detector. The X-ray arrays can be swiveled around a common swiveling axis within whose range an object is locatable. The X-ray detectors are situated opposite the X-ray sources with respect to the swiveling axis. They are embodied as flat-panel detectors so that an irradiating of the object in a first or, as the case may be, second irradiation plane can be registered by them. The irradiation planes contain the swiveling axis and run perpendicular to connecting lines linking the X-ray sources to the X-ray detectors. The area contents of the irradiation planes are mutually different. When the X-ray arrays are positioned correspondingly, the first irradiation plane will completely cover the second irradiation plane.

24 Claims, 5 Drawing Sheets

X-RAY SYSTEM HAVING A FIRST AND A SECOND X-RAY ARRAY

CROSS REFERENCE TO RELATED APPLICATIONS

This application claims priority to the German application No. 10 2004 061 933.6, filed Dec. 22, 2004 which is incorporated by reference herein in its entirety.

FIELD OF INVENTION

The present invention relates to an X-ray system having a first and a second X-ray array
wherein the first X-ray array has a first X-ray source and a first X-ray detector,
wherein the second X-ray array has a second X-ray source and a second X-ray detector,
wherein the X-ray arrays can be swiveled around a common swiveling axis within whose range an object is locatable,
wherein the X-ray detectors are situated opposite the X-ray sources with respect to the swiveling axis,
wherein the X-ray detectors are embodied as flat-panel detectors so that an irradiating of the object in a first irradiation plane can be registered using the first X-ray detector and an irradiating of the object in a second irradiation plane can be registered using the second X-ray detector,
wherein the irradiation planes contain the swiveling axis and run perpendicular to a connecting line linking the first X-ray source to the first X-ray detector or, as the case may be, linking the second X-ray source to the second X-ray detector.

BACKGROUND OF INVENTION

X-ray systems of such type are known. The applicant is aware that they are employed to irradiate an object (as a rule a person) from two different directions simultaneously (what is termed biplane operation) and thus to register quasi three-dimensional information about said object. The applicant is not aware that X-ray systems of such type are also employed to establish realtime three-dimensional reconstructions of the object.

X-ray systems having a single X-ray array are also known within the prior art in which systems the X-ray array has an X-ray source and an X-ray detector and the X-ray array can be swiveled around a swiveling axis within whose range an object is locatable. The X-ray detector is in this case, too, located opposite the X-ray source with respect to the swiveling axis. Said X-ray detector is embodied as a flat-panel detector so that an irradiating of the object in an irradiation plane containing the swiveling axis and running perpendicular to a connecting line linking the X-ray source to the X-ray detector can be registered using said X-ray detector.

For X-ray systems of this type, usually embodied as what are termed C-arc systems, it is generally known that they can also be employed for registering a number of projections of the object while the X-ray array is being swiveled around the swiveling axis and for establishing a three-dimensional reconstruction of the object based on the registered projections. Said procedure is frequently employed particularly in the field of angiography.

SUMMARY OF INVENTION

If, when the projections have been registered, interventional operations are performed on the object along with the corresponding establishing of the three-dimensional reconstruction thereof, it is possible that the object will be deformed, for example through the insertion of medical instruments. Fast updating of the three-dimensional reconstruction at least at the site of intervention is thus of major advantage.

An object of the present invention is to provide an X-ray system by means of which both the initial production of the object's three-dimensional reconstruction and updating of its three-dimensional reconstruction are possible in a simple manner. A further object of the present invention is to disclose suitable operating methods for the correspondingly embodied X-ray system.

The first object is achieved in an X-ray system of the type mentioned at the beginning by embodying the X-ray arrays in such a way that the area content of the second irradiation plane is smaller than the area content of the first irradiation plane and that, when the X-ray arrays are positioned correspondingly, the first irradiation plane will completely cover the second irradiation plane.

Said embodiment of the X-ray system is optimized for the initial establishment of the object's three-dimensional reconstruction because, as a result of the X-ray system's being appropriately driven by a control device, the first X-ray array can in this case be swiveled around the swiveling axis through an advance swiveling-angle range, with its being possible during swiveling for a number of two-dimensional advance projections of the object to be registered exclusively by means of the first X-ray detector at registering angles and routed to the control device, and for the object's three-dimensional reconstruction then to be established by the control device exclusively on the basis of the advance projections registered using the first X-ray detector. Owing to the use only of the first X-ray detector for registering the two-dimensional advance projections, the object can be reconstructed over a sufficiently large volume range.

For subsequent updating operations, deformations and other changes in the object will in all probability occur only within a pre-known small volume range. For subsequent updating of the object's three-dimensional reconstruction it will thus suffice for the projections only to be recorded in a smaller planar area. The second X-ray detector will thus suffice for this. Moreover, the combination of two differently sized irradiation planes will allow greater flexibility in terms of the positioning of the X-ray arrays.

Through reducing the size of the second X-ray array it is furthermore often possible to lessen the object's (=person's) exposure to X-radiation while the X-ray system is operating. It may even be possible and of practical benefit to operate the first X-ray detector only in a part of its registering range during subsequent updating of the three-dimensional reconstruction so that the first irradiation plane will in this case be reduced to a partial area preferably congruent to the second irradiation plane.

The first X-ray array can preferably alternatively be swiveled around the swiveling axis either together with the second X-ray array or without the second X-ray array. That is because at least smaller moved masses will result therefrom when the first X-ray array is swiveled on its own. Both coupled and decoupled operation of the X-ray arrays is furthermore possible in this case.

Swiveling of the first X-ray array alternatively together with the second X-ray array or without the second X-ray array is particularly easy to implement owing to the possibility of putting the second X-ray array into an operating position for swiveling together with the first X-ray array and of removing it from the operating position for solitary swiveling of the first X-ray array around the swiveling axis, with its here being alternatively possible to remove the second X-ray array from the operating position by moving it into a parked position or detaching it from the X-ray system.

Removing the second X-ray array from the operating position is of practical benefit particularly because the first X-ray array can in many cases be swiveled through a larger angle range when the second X-ray array has been removed from the operating position than when the second X-ray array is in the operating position.

The first irradiation plane is preferably greater in extent than the second irradiation plane both in the direction of the swiveling axis and diagonally thereto. The area content of the first irradiation plane is furthermore preferably at least twice as large as the area content of the second irradiation plane.

The X-ray system according to the invention can, as already mentioned, preferably be operated in such a way that as a result o f the X-ray system's being appropriately driven by a control device the first X-ray array is swiveled around the swiveling axis through an advance swiveling-angle range, a number of two-dimensional advance projections of the object are registered during swiveling exclusively by means of the first X-ray detector at registering angles and routed to the control device, and a three-dimensional reconstruction of the object is established by the control device exclusively on the basis of the advance projections registered using the first X-ray detector, with (depending on how the X-ray system is embodied) the second X-ray array being, where applicable, removed from its operating position before the first X-ray array is swiveled around the swiveling axis and returned to its operating position once the two-dimensional advance projections have been registered.

It will in many cases suffice following initial establishment of the object's three-dimensional reconstruction to position the X-ray arrays in such a way that they register two-dimensional live projections of the object from different projection directions and that the registered two-dimensional live projections are routed to the control device, with the X-ray arrays preferably (though not of necessity) being positioned to in each case one of the registering angles at which the two-dimensional advance projections were previously registered.

Quasi three-dimensional live information about the object will be available to the operator of the X-ray system thanks to the procedure last described above in addition to the three-dimensional reconstruction of the object established in advance. Yet it would be even better if the three-dimensional reconstruction could itself be updated. To make this possible, too, it has been provided for the control device to determine on the basis of the two-dimensional live projections whether the object has changed and, if it has, to update its three-dimensional reconstruction using the two-dimensional live projections of both X-ray arrays.

It can be determined whether the object has changed by comparing the live projections with previously recorded two-dimensional projections of the object. However, an alternative possibility is for two-dimensional reconstruction projections corresponding to the live projections to be established by the control device using the object's three-dimensional reconstruction and for it to be determined whether the object has changed by comparing the two-dimensional live projections with the two-dimensional reconstruction projections.

For updating the object's three-dimensional reconstruction, at in each case at least one of the registering angles in each case one live projection is registered using the first and the second X-ray array, the corresponding advance projections are updated using the registered live projections, and the object's updated three-dimensional reconstruction is established by the control device using the updated advance projections, where applicable augmented to include the non-updated advance projections. This procedure is possible in particular because any changes to the object outside the area covered by the two X-ray detectors are extremely improbable.

For updating the object's three-dimensional reconstruction it is necessary to update the advance projections. It can in individual cases here suffice to update in each case precisely one of the advance projections with the live projection registered using the first X-ray array or, as the case may be, the second X-ray array. As a rule, however, for updating the advance projections the X-ray arrays are simultaneously swiveled through a live swiveling-angle range around the swiveling axis, in each case one live projection is registered using the first and the second X-ray array at in each case at least two of the registering angles, and the corresponding advance projections are updated using the live projections registered by the X-ray arrays. It broadly suffices here if the live swiveling-angle range is less than half the size of the advance swiveling-angle range.

The advance projections updated using the live projections registered by means of the second X-ray array are preferably updated exclusively within the second irradiation plane. The remainder of the relevant advance projections are retained unchanged. That is because a particularly good reconstruction having in particular no or only few artifacts is facilitated thereby as it takes place via the "large", merely updated advance projections.

If a partial volume is selected within the object's three-dimensional reconstruction, an area of the object corresponding to the partial volume is registered by means both of the first and of the second X-ray array, and the three-dimensional reconstruction is updated only within the partial volume, then updating of the three-dimensional reconstruction will be possible with especially little computing effort. The partial volume can therein be selected by an operator.

If, with the aid of the live projections, a site is identified within the space at which site is located an instrument that has been inserted into the object, and if said site is accordingly marked in a two-dimensional reconstructed representation established using the object's three-dimensional reconstruction, then it will be made significantly easier for an operator of the X-ray system to intellectually comprehend the information shown.

The result will be similar if a corresponding two-dimensional reconstruction projection is established by the control device with regard to at least one of the live projections and the at least one live projection is fed out to an operator in addition to or together with the two-dimensional reconstruction projection.

BRIEF DESCRIPTION OF THE DRAWINGS

Further advantages and specifics will emerge from the following description of an exemplary embodiment in conjunction with the drawings.

DETAILED DESCRIPTION OF INVENTION

Figure 1:
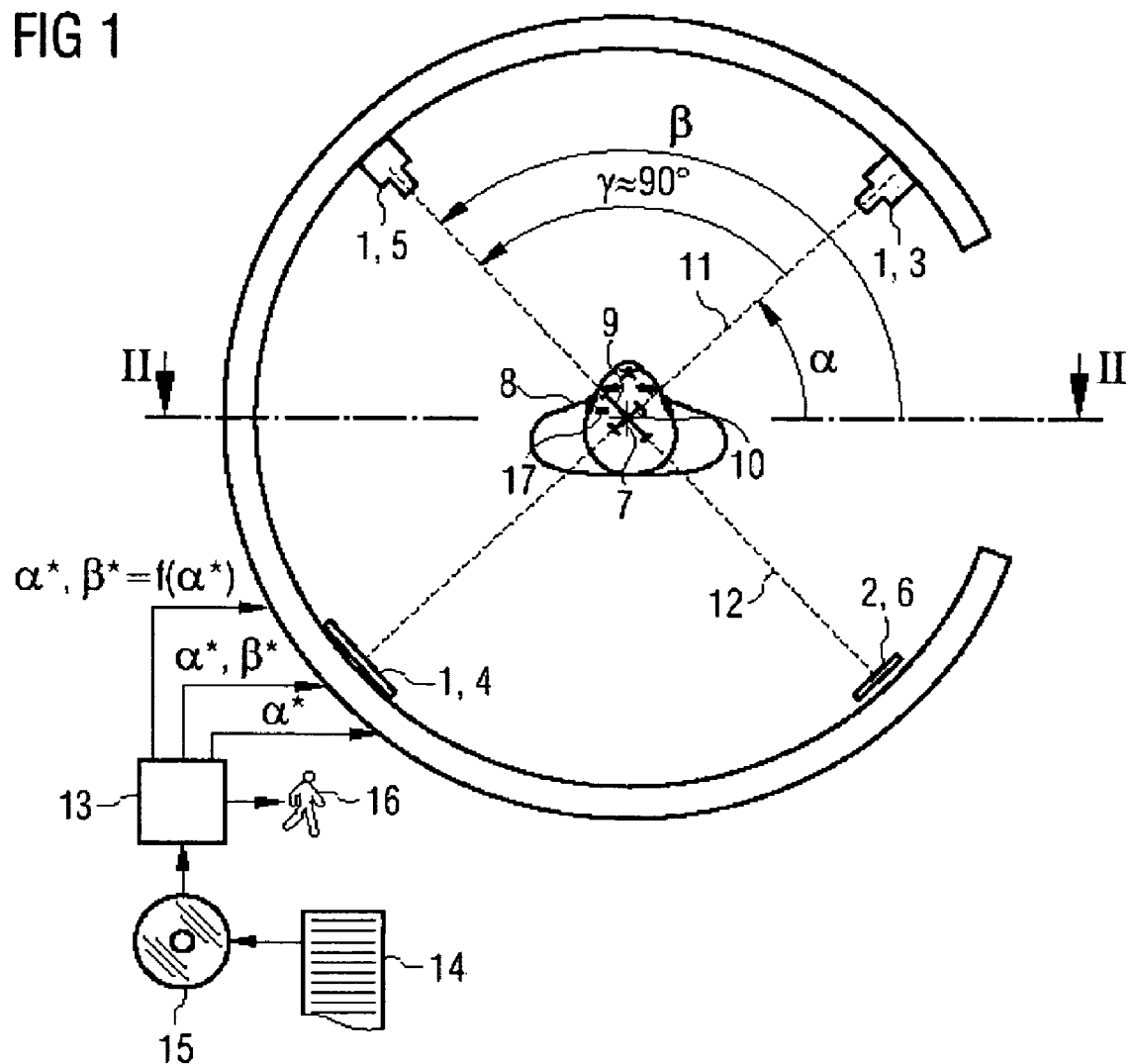
FIG. 1 is a schematic lateral view of an X-ray system according to the invention.

According to FIG. 1 an X-ray array has a first X-ray array 1 and a second X-ray array 2. The first X-ray array 1 has a first X-ray source 3 and a first X-ray detector 4. The second X-ray array 2 likewise has a second X-ray source 5 and a second X-ray detector 6. The X-ray arrays 1, 2 can be swiveled around a common swiveling axis 7. As can be seen, the X-ray detectors 4, 6 are therein situated opposite the X-ray sources 3, 5 with respect to the swiveling axis 7. An object 8, for example a person 8 indicated schematically as such in FIG. 1, is locatable in the range of the swiveling axis 7.

Figure 2:
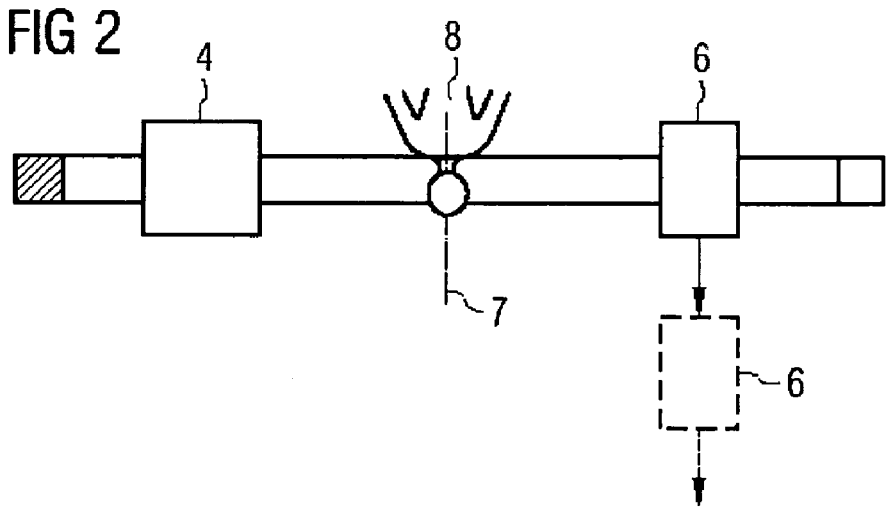
FIG. 2 is a top view of the X-ray system shown in FIG. 1.
Figure 3:
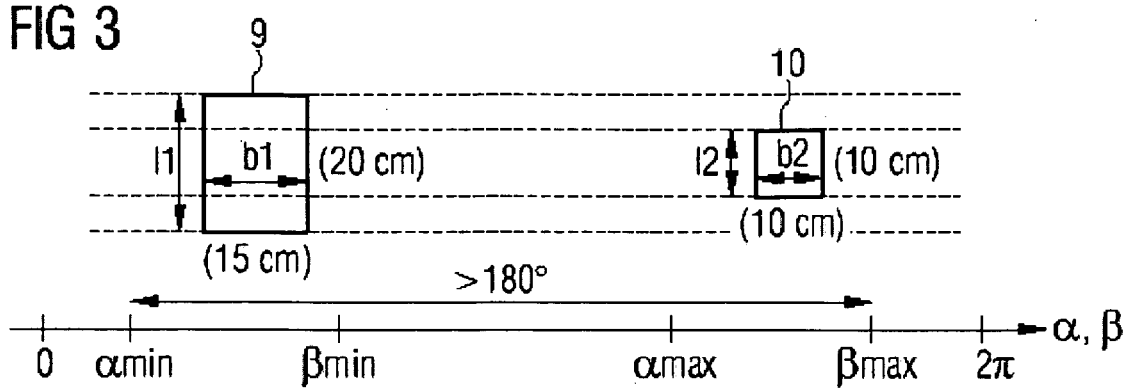
FIG. 3 is an uncoiled representation of a swivel area.

As is especially apparent from FIGS. 2 and 3, the X-ray detectors 4, 6 are embodied as flat-panel detectors 4, 6. An irradiating of the object 8 in a first irradiation plane 9 can thereby be registered using the first X-ray detector 4, and an irradiating of the object 8 in a second irradiation plane 10 can be registered using the second X-ray detector 6.

The irradiation planes 9, 10 contain the swiveling axis 7. The first irradiation plane 9 furthermore runs perpendicular to a connecting line 11 which in turn runs from the first X-ray source 3 to the first X-ray detector 4. The second irradiation plane 10 furthermore in turn runs perpendicular to a connecting line 12 itself running from the second X-ray source 5 to the second X-ray detector 6, with the connecting lines 11, 12 each passing through the center of the X-ray sources 3, 5 and the center of the X-ray detectors 4, 6.

A swivel area of the X-ray arrays 1, 2 is illustrated uncoiled in FIG. 3. As can be seen, the first irradiation plane 9 has in the direction of the swiveling axis 7 a longitudinal extent 11 that is larger than the corresponding longitudinal extent 12 of the second irradiation plane 10. Also diagonally to the swiveling axis 7 the first irradiation plane 9 has, as can be seen, a larger transverse extent b1 than the second irradiation plane 10. It is preferably ensured thereby that the area content of the first irradiation plane 9 is at least twice as large as the area content of the second irradiation plane 10. That will be the case when, for example, the longitudinal extents 11, 12 are 20 and 10 cm and the transverse extents b1, b2 are 15 and 10 cm, but the area content of the second irradiation plane 10 should in any event be smaller than the area content of the first irradiation plane 9.

As can further be seen from FIG. 3, there are corresponding positions of the X-ray arrays 1, 2 at which the first irradiation plane 9 will entirely cover the second irradiation plane 10. The aim and purpose of this embodiment will become apparent as this description proceeds.

The X-ray sources 3, 5 and the X-ray detectors 4, 6 (see FIG. 1) can as a rule be swiveled around the swiveling axis 7 along a common orbit. The irradiation planes 9, 10 thus correspond to a centric elongation of the corresponding X-ray detectors 4, 6 having the factor 0.5 and the X-ray sources 3, 5 as elongation centers. The X-ray detectors 4, 6 therefore have twice the dimensions and four times the area content of the corresponding irradiation planes 9, 10.

The X-ray system is controlled by a control device 13. The operating mode of said control device 13 is in turn determined by a control program 14. After being created, the control program 14 is initially stored on a data medium 15, for example on a CD-ROM 15. Said program is routed in this exemplary manner to the control device 13 via the data medium 15.

Through being programmed by means of the control program 14, the control device 13 is able, for example, to swivel the first and the second X-ray array 1, 2 around the swiveling axis 7 simultaneously. In this case the X-ray arrays 1, 2 will while being swiveled retain an offset angle $\gamma$ that is usually about 90°, although another offset angle $\gamma$ is also basically possible.

Furthermore, when the X-ray arrays 1, 2 are arranged statically, the two X-ray arrays 1, 2 will as a rule be positioned in such a way that the object 8 will be irradiated once substantially horizontally and once substantially vertically, although other embodiments are also possible here, for example the diagonal irradiation shown in FIGS. 1 and 2.

Simultaneous swiveling of the X-ray arrays 1, 2 around the swiveling axis 7 can alternatively be on a coupled or an uncoupled basis.

Coupled swiveling is indicated in FIG. 1 by the fact that the control device 13 is able to feed out a first setpoint angle value $\alpha^*$ to the first X-ray array 1 and simultaneously a second setpoint angle value $\beta^*$ to the second X-ray array 2, with the second setpoint angle value $\beta^*$ being a function f of the first setpoint angle value $\alpha^*$. The second setpoint angle value $\beta^*$ can in particular differ from the first setpoint angle value $\alpha^*$ only by the offset angle $\gamma$.

Uncoupled simultaneous swiveling of the X-ray arrays 1, 2 is indicated in FIG. 1 by the fact that the control device 13 is also able to feed out both setpoint angle values $\alpha^*$, $\beta^*$, but that the second setpoint angle value $\beta^*$ does not have a functional relationship with the first setpoint angle value $\alpha^*$.

It is furthermore possible for only the first X-ray array 1 to be driven by the control device 13. This is indicated in FIG. 1 by the fact that only the first setpoint angle value $\alpha^*$ is fed out. In this case, therefore, the first X-ray array 1 is swiveled without the second X-ray array 2.

The X-ray sources 3, 5 and the X-ray detectors 4, 6 can, as already mentioned, as a rule be swiveled around the swiveling axis 7 along a common orbit. The second X-ray array 2 may hence impede the swiveling of the first X-ray array 1. This will most particularly be the case when the second X-ray array 2 is not swiveled around the swiveling axis 7 at all but instead held at a fixed angle position. The first X-ray array 1 can, however, also be affected even if the second X-ray array 2 is swiveled together with the first X-ray array 1.

For example, FIG. 3 shows that the first X-ray array 1 can be swiveled toward small angles always up to a first minimum angle $\alpha$min. If the second X-ray array 2 is in an operating position (indicated in FIG. 2 for the second X-ray detector 6 by means of continuous lines), then the first X-ray array 1 can be swiveled toward large angles up to a first maximum angle $\alpha$max. Corresponding to the swiveling ability of the first X-ray array 1, the second X-ray array 2 can be swiveled between a second minimum angle $\beta$min and a second maximum angle $\beta$max.

If, by contrast, the second X-ray array 2 is removed from its operating position, then it will be possible to swivel the first X-ray array 1 not just up to the first maximum angle $\alpha$max but up to the second maximum angle $\beta$max, the end result thus being swiveling through a larger angle range. In many operating conditions (see below) it will therefore be advantageous if the second X-ray array, though being positioned in its operating position for swiveling together with the first X-ray array 1, is removed from its operating position to allow solitary swiveling of the first X-ray array 1 around the swiveling axis 7. The second X-ray array 2 can, for example, for this purpose be put from its operating position into a parked position, indicated in FIG. 2 for the second X-ray detector 6 by means of dashing lining. The second X-ray array 2 can be put from its operating position into the parked position and vice versa either manually or under the motorized control of the control device 13. It is alternatively also possible to remove the second X-ray array 2 from its operating position by detaching it from the X-ray system. This is indicated in FIG. 2 by means of a dashed arrow extending beyond the parked position. Detaching of said type must of course be performed manually.

The X-ray system embodied according to the invention is, when controlled by the control device 13, also operable in an intrinsically inventive manner. This is explained in more detail below in conjunction with FIGS. 4 to 9.

Figure 4:
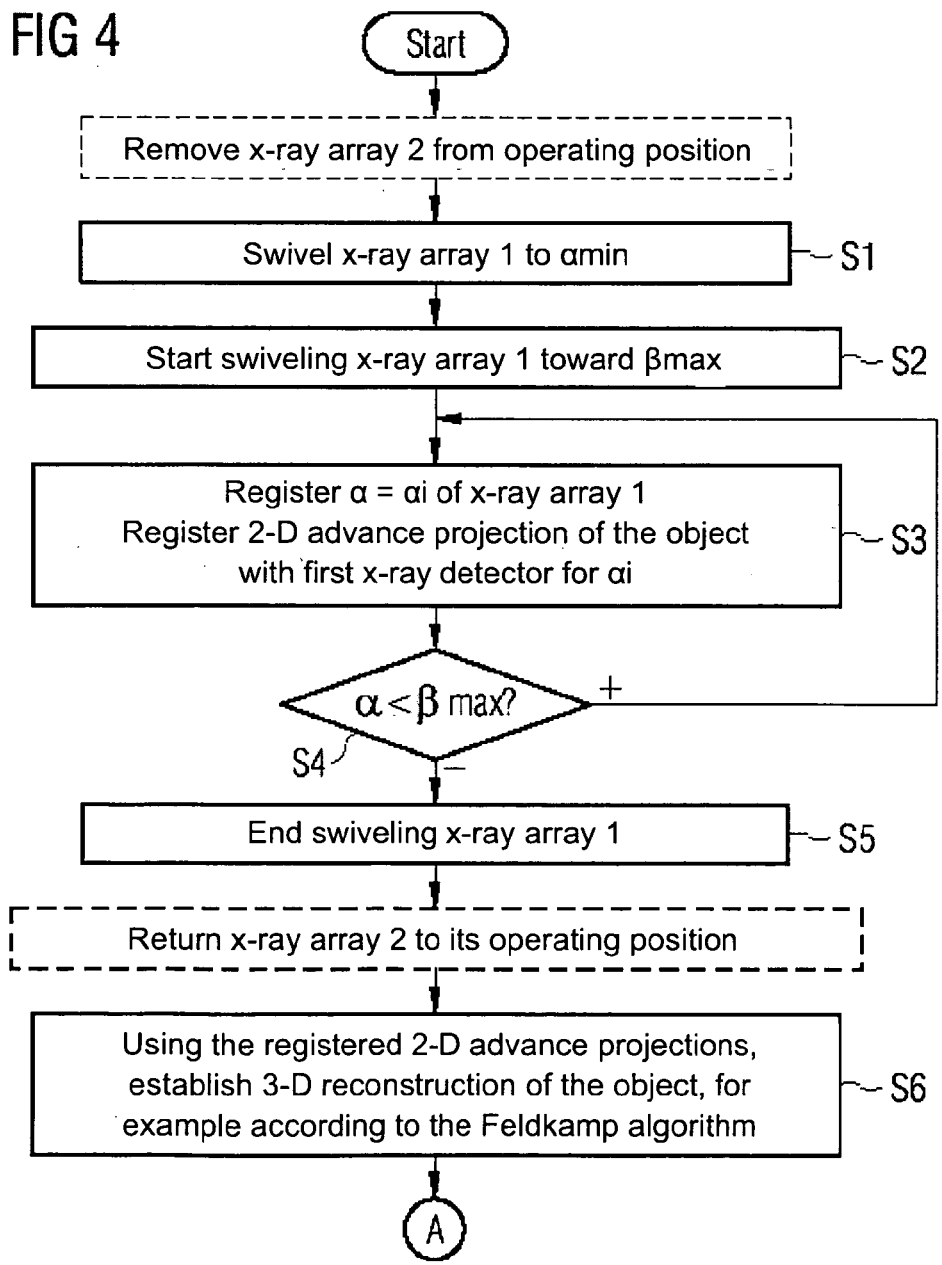
FIGS. 4 to 9 are flowcharts.

According to FIG. 4, the control device 13 initially registers the angle position of the first X-ray array 1 in a step S1 then swivels said array, where applicable, to the first minimum angle $\alpha$min. If necessary, the second X-ray array 2 will first be removed from its operating position. Since, however, this step (removing the second X-ray array 2 from its operating position) is not essential, it is only shown by means of dashed outlining in FIG. 4 and has not been provided with it s own reference numeral. The control device 13 then begins in a step S2 to swivel the first X-ray array 1 around the swiveling axis 7 and to perform steps S3 and S4 iteratively.

In step S3 the control device 13 takes over in each case one two-dimensional advance projection from the first X-ray detector 4 by which it was registered immediately before. The control device 13 stores the advance projection routed to it along with the momentary registering angle $\alpha$i at which the advance projection was registered. The control device 13 checks in step S4 whether the first X-ray array 1 has already reached, for example, the second maximum angle $\beta$max. Until that is the case the control device 13 will keep returning to step S3.

If, by contrast, it is determined in step S4 that the second maximum angle $\beta$max (or another, pre-specified angle) has been reached, the control device 13 will proceed to a step S5. The control device 13 terminates swiveling of the first X-ray array 1 in said step S5. In a step S6 the control device 13 will then establish a three-dimensional reconstruction of the object 8 using the advance projections registered using the first X-ray detector 4.

Within the scope of steps S2 to S5 the first X-ray array 1 is thus swiveled through an advance swiveling-angle range around the swiveling axis 7. The advance swiveling-angle range must of course have been suitably specified. If the reconstruction in step S6 is to take place according to, for example, the generally known Feldkamp algorithm, then the advance swiveling-angle range must be at least 180°.

If removed from its operating position at the start of the flow of operations shown in FIG. 4, the second X-ray array 2 will now be returned to its operating position. This can be done either before or after the three-dimensional reconstruction of the object 8 has been established, but in any event after all advance projections have been registered. If necessary, the first X-ray array 1 is furthermore swiveled out of the angle range between the first and the second maximum angle $\alpha$max, $\beta$max before the second X-ray array 2 is returned to its operating position.

Regardless of whether the second X-ray array 2 remains in its operating position or not, the advance projections will be registered exclusively by means of the first X-ray detector 4. The three-dimensional reconstruction of the object 8 will thus also be established exclusively using the advance projections registered by means of the first X-ray detector 4 since no advance projections are registered by means of the second X-ray detector 6.

The advance projections are, as already mentioned, two-dimensional projections. They differ from live projections to be introduced later only in being registered in advance so that said advance projections can then be used to carry out the three-dimensional reconstruction of the object 8. The terms "advance" and "in advance" as used herein have no further meaning.

Figure 5:
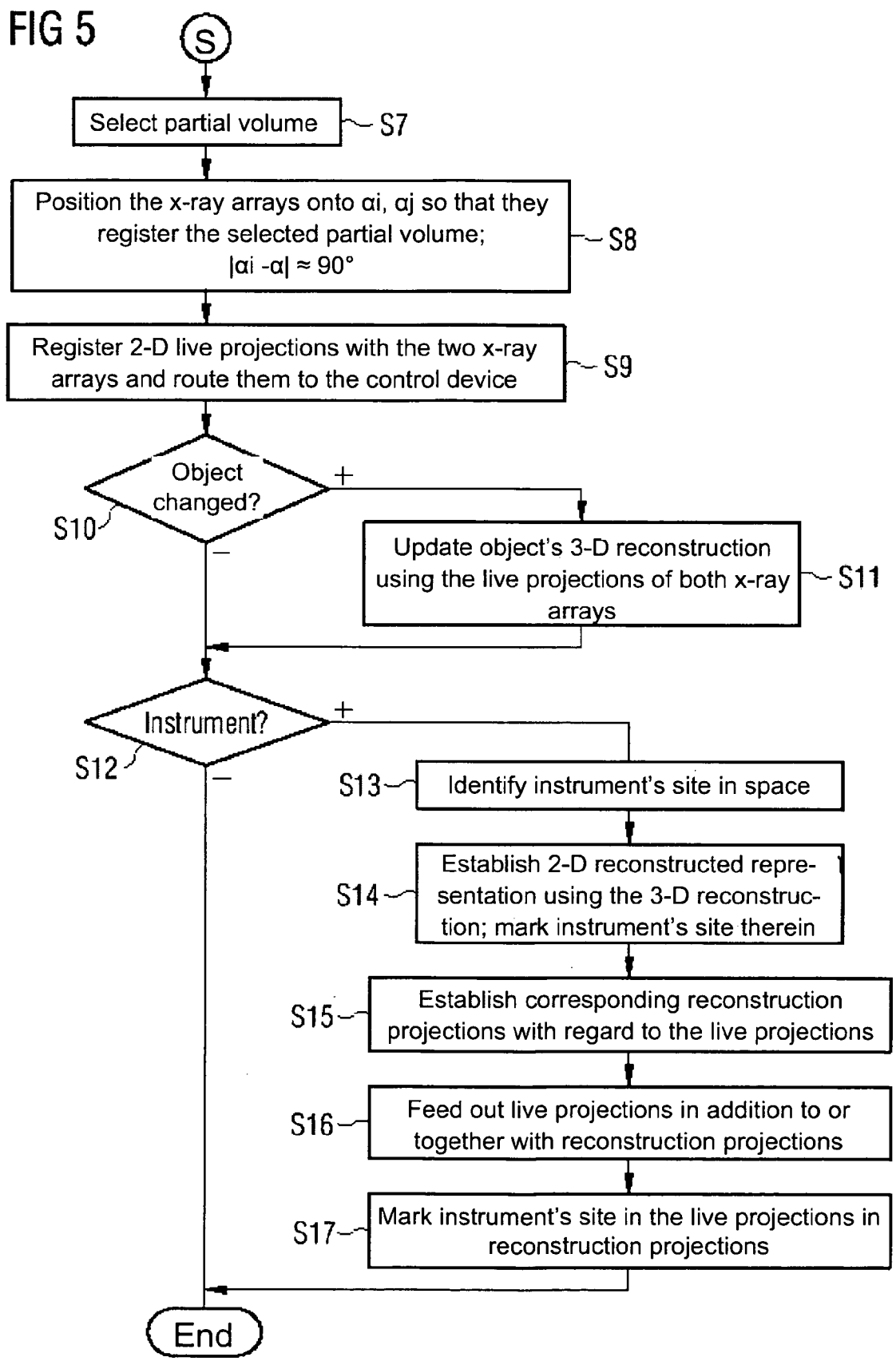

When the three-dimensional reconstruction of the object 8 has been established, a partial volume is selected within said three-dimensional reconstruction according to FIG. 5 in a step S7. Said partial volume can be selected according to FIG. 5 by an operator 16, who indicates to the control device 13 how the partial volume has been defined. The X-ray arrays 1, 2 are then positioned in a step S8, either manually or by means of the control device 13, in such a way that the two X-ray arrays 1, 2 each register an area of the object 8 corresponding to the previously selected partial volume. The X-ray arrays 1, 2 are furthermore preferably positioned in step S8 to in each case one of the registering angles $\alpha$i, $\alpha$j. The X-ray arrays 1, 2 are furthermore as a rule positioned in such a way that the difference in the registering angles $\alpha$i, $\alpha$j to which the first or, as the case may be, second X-ray array 1, 2 is positioned is about 90°.

When the X-ray arrays 1, 2 have been positioned their X-ray detectors 4, 6 will be able to register two-dimensional live projections of the object 8 from different projection directions and route the registered two-dimensional live projections to the control device 13. Said control device 13 feeds out the live projections to the operator 16 via a display device. Referring to said projections as live projections serves on the one hand to distinguish them in terminology terms from the advance projections already introduced and, on the other hand, to make it clear through the choice of word that said live projections are current projections of the object 8 being irradiated at this instant. Registering of the live projections by the X-ray detectors 4, 6 and taking over of the live projections by the control device 13 are operations that are performed according to FIG. 5 in a step S9.

The control device 13 then determines in a step S10 whether the object 8 has changed, doing so using the two-dimensional live projections registered in step S8. If the control device 13 establishes in said step S10 that the object 8 has changed, then the next step will be step S11, in which the control device 13 updates the three-dimensional reconstruction of the object 8 using the two-dimensional live projections of both X-ray arrays 1, 2.

The control device 13 checks in a step S12 whether the registered live projections contain the image of an instrument 17 (shown schematically in FIG. 1) that has been inserted into the object 8. This can be done by, for example, identifying an area within the live projections that is particularly rich in contrast compared with its surrounding area. This procedure is known per se.

If an instrument 17 of said type has been identified in both live projections, then the control device 13 will in a step S13 proceed to use both live projections to determine a site within the space at which said instrument 17 is located. This is possible because the instrument 17 can be isolated in both live projections and, in a manner akin to a cross-bearing operation, the site of said instrument 17 within the space then determined. It is possible thereby in a step S14 to use the three-dimensional reconstruction of the object 8 to establish a two-dimensional reconstructed representation and feed this out to the operator 16 and mark the site of the instrument 17 therein.

The reconstructed representation can, in common with the advance projections and live projections, be a perspective projection. However, in contrast to the advance projections and live projections it can also be a parallel projection or sectional representation. What is decisive is for it to be established using the three-dimensional reconstruction of the object 8, not the object 8 itself.

As an alternative or in addition to marking the site of the instrument 17 it is also possible for a corresponding two-dimensional reconstruction projection to be established by the control device 13 in a step S15 (as a special instance of a reconstructed representation) with regard to at least one of the live projections and in a step S16 for the at least one live projection to be fed out to the operator 16 in addition to or together with the reconstruction projection. It is also possible for a site within the live projection at which site the instrument 17 is located to be marked in a step S17 in the corresponding reconstruction projection. In this case the reconstruction projection must of course be established using the same imaging parameters as the corresponding live projection.

Since in this case the live projection or, as the case may be, live projections and the reconstruction projection or, as the case may be, reconstruction projections will mutually correspond, for this procedure it is not absolutely essential to evaluate both live projections. That will, however, as a rule be done.

Various procedures are possible for determining whether the object 8 has changed. The same applies to the updating of the three-dimensional reconstruction of the object 8.

Figure 6:
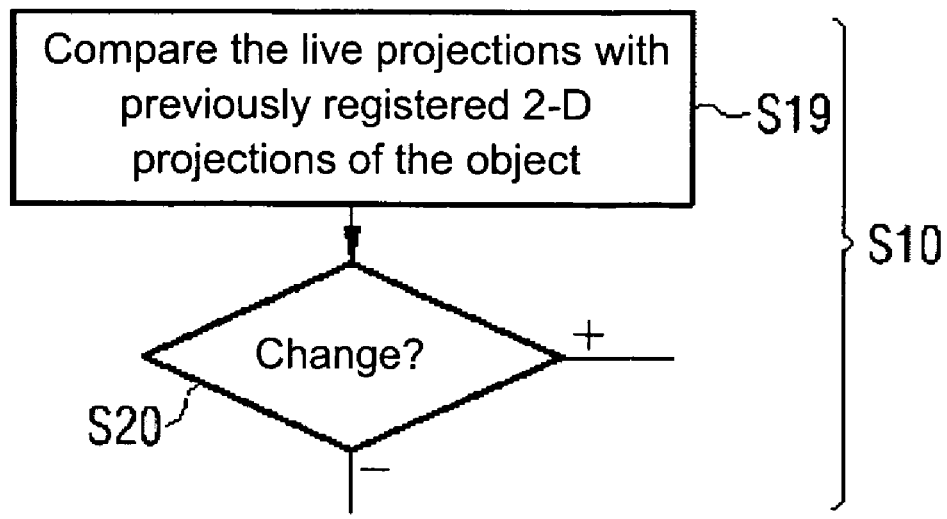
Figure 7:
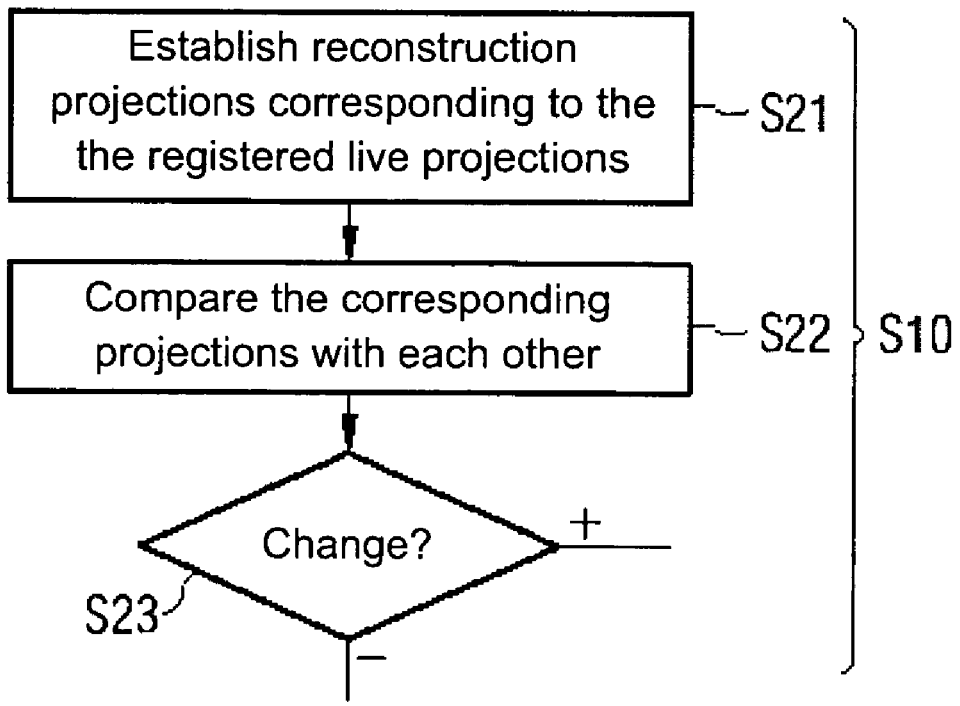

Thus according to FIG. 6 it is possible, for example, employing an embodiment of step S10 in FIG. 5 to compare the live projections currently being registered with previously registered, buffered projections of the object 8 in a step S19. The previously buffered projections of the object 8 can therein in particular be the live projections registered immediately before or the corresponding advance projections. If the object 8 has not changed and projection parameters of the X-ray arrays 1, 2 have remained unchanged, then the older projections should be identical to the more recent ones. There can in practice be a deviation around a (small!) bound. Using the comparison it can thus be decided in a step S20 whether the live projections, and hence the object 8, have changed.

According to FIG. 7, again employing an embodiment of step S10 in FIG. 5, it is alternatively possible, for example, for the control device 13 in a step S21 to use the three-dimensional reconstruction of the object 8 initially to establish reconstruction projections corresponding to the two-dimensional live projections. Incidentally, step S15 in FIG. 5 can, where applicable, be simplified accordingly in this case.

These reconstruction projections should also ideally tally with the live projections. It is thus possible to compare the reconstruction projections and corresponding live projections with each other in a step S22. Depending on the result of the comparison, it will then be possible to branch from a step S23 to step S11 in FIG. 5 or directly to step S12 in FIG. 5.

It can in individual cases suffice for updating the three-dimensional reconstruction of the object 8 if in each case precisely one of the advance projections is updated by the live projections registered using the first X-ray array 1 or, as the case may be, second X-ray array 2. The two advance projections requiring to be updated have of course been determined by the two registering angles αi, βj at which the X-ray arrays 1, 2 are positioned. That is the precise reason, among others, why the X-ray arrays 1, 2 were positioned in step S8 in FIG. 5 to be exactly at the registering angles αi, αj.

Figure 8:
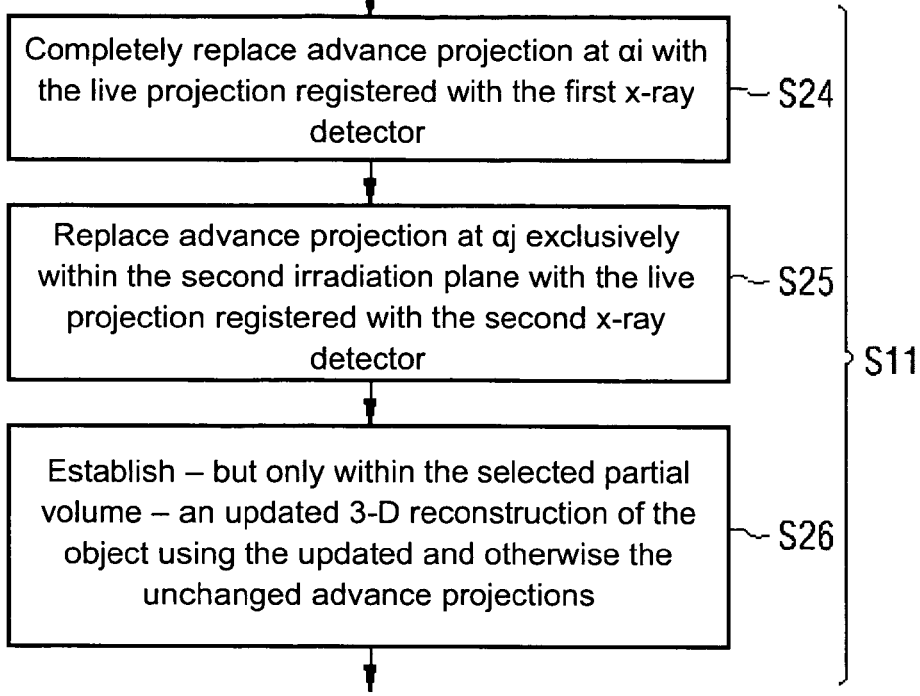
Figure 9:
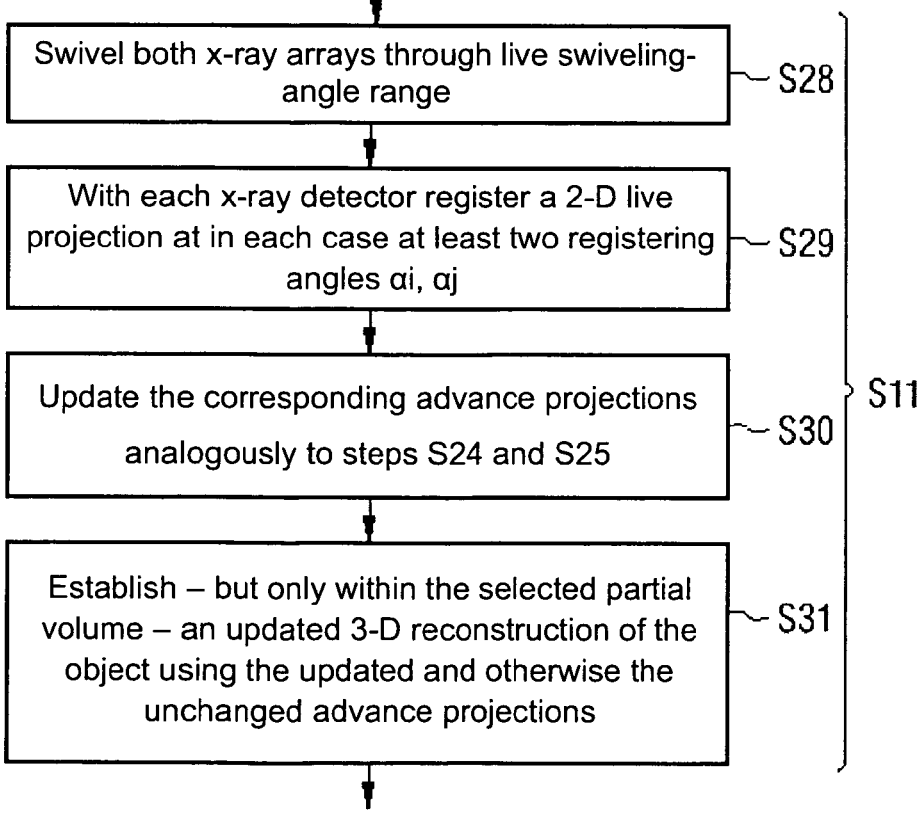

If it suffices to update in each case precisely one advance projection, then according to FIG. 8 the advance projection corresponding to the live projection registered using the first X-ray detector 4 will be completely replaced in a step S24 by the live projection registered using the first X-ray detector 4. The advance projection updated using the live projection registered using the second X-ray detector 6 will, by contrast, be updated in a step S25 exclusively within the second irradiation plane 10. Outside the second irradiation plane 10 it will be retained in unchanged form.

A (now updated) three-dimensional reconstruction of the object 8 is then established again in a step S26. However, the three-dimensional reconstruction of the object 8 is preferably established only within the previously selected partial volume. That is because it can straight away be assumed that no changes have taken place in the rest of the object 8. The computing effort needed to establish the three-dimensional reconstruction can consequently be substantially reduced. A further partial area can, where applicable, even be singled by the operator 16 within the partial volume. The three-dimensional reconstruction will in this case even only be updated within the partial area.

As a rule, though, more than two updated advance projections are required for updating the three-dimensional reconstruction of the object 8. So as a rule (see FIG. 9), both X-ray arrays 1, 2 are in a step S28 simultaneously swiveled through a live swiveling-angle range around the swiveling axis 7 for updating the three-dimensional reconstruction of the object 8. The live swiveling-angle range is as a rule significantly smaller than the advance swiveling-angle range. In particular it is as a rule less than half the size of the advance swiveling-angle range. It can, for example, be a third, a quarter, a fifth etc. of the advance swiveling-angle range. It can be either permanently assigned or assigned to the control device 13 by the operator 16.

While the X-ray arrays 1, 2 are being swiveled through the live swiveling-angle range, in each case one live projection is registered in a step S29 using the first and second X-ray array 1, 2 at in each case at least two of the registering angles αi, αj. The live projections thus registered are routed to the control device 13 which, in a step S30, then establishes and updates the corresponding advance projections. Updating of the advance projections in step S30 is carried out analogously to the procedure for steps S24 and S25 in FIG. 8.

The updated three-dimensional reconstruction of the object 8 is then established in a step S31. Said step S31 corresponds to step S26 in FIG. 8. The only difference is that in this case there are more than two updated advance projections.

The X-ray system according to the invention thus facilitates both optimized initial establishing of the three-dimensional reconstruction of the object 8 and efficient live irradiating of the object 8, as well as fast and simple updating of the three-dimensional reconstruction of the object 8 if the object 8 has changed.

The invention claimed is:

1. An X-ray system, comprising first and second X-ray arrays, the first X-ray array having a first X-ray source and a first X-ray detector, the second X-ray array having a second X-ray source and a second X-ray detector,
   wherein the first and second X-ray arrays are configured to:
   be swiveled around a common swiveling axis, and
   arrange an examination object within a range related to the swiveling axis, wherein the first and second X-ray detectors are:
arranged opposite the X-ray sources relative to the swiveling axis, and
embodied as flat-panel detectors, such that irradiating the object is registered relative to a first irradiation plane using the first X-ray detector and relative to a second irradiation plane using the second X-ray detector,
wherein the first and second irradiation planes:
include the swiveling axis, and
run perpendicular to a connecting line linking the first X-ray source to the first X-ray detector or the second X-ray source to the second X-ray detector,
wherein:
a surface area of the second irradiation plane is smaller than a surface area of the first irradiation plane, and
the first irradiation plane completely covers the second irradiation plane, and
wherein the first X-ray array is configured to alternatively be swiveled around the swiveling axis either together with the second X-ray array or without the second X-ray array, and
wherein:
the second X-ray array is configured to be put into an operating position for swiveling together with the first X-ray array, and
the second X-ray array is removed from the operating position for swiveling only the first X-ray array around the swiveling axis.

2. The X-ray system according to claim 1, wherein the second X-ray array is removed from the operating position into a parking position.

3. The X-ray system according to claim 1, wherein the second X-ray array is removed from the operating position by detaching the second X-ray array from the X-ray system.

4. The X-ray system according to claim 1, wherein the first X-ray array is swiveled through a larger angle range when the second X-ray array is removed from the operating position compared to the second X-ray array arranged in the operating position.

5. An X-ray system, comprising:
a first and a second X-ray arrays, the first X-ray array having a first X-ray source and a first X-ray detector, the second X-ray array having a second X-ray source and a second X-ray detector,
wherein the first and second X-ray arrays are configured to:
be swiveled around a common swiveling axis, and
arrange an examination object within a range related to the swiveling axis,
wherein the first and second X-ray detectors are:
arranged opposite the X-ray sources relative to the swiveling axis, and
embodied as flat-panel detectors, such that irradiating the object is registered relative to a first irradiation plane using the first X-ray detector and relative to a second irradiation plane using the second X-ray detector,
wherein the first and second irradiation planes:
include the swiveling axis, and
run perpendicular to a connecting line linking the first X-ray source to the first X-ray detector or the second X-ray source to the second X-ray detector,
wherein:
a surface area of the second irradiation plane is smaller than a surface area of the first irradiation plane, and
the first irradiation plane completely covers the second irradiation plane; and
a control device that controls the first X-ray array being swiveled around the common swiveling axis simultaneously with the second X-ray array or solitarily without the second X-ray array,
wherein the first irradiation plane has a greater extent than the second irradiation plane relative to both a direction of the swiveling axis and a direction diagonally to the direction of the swiveling axis.

6. The X-ray system according to claim 5, wherein the surface area of the first irradiation plane is at least twice the surface area of the second irradiation plane.

7. The X-ray system according to claim 5, wherein the control device controls the first X-ray array being swiveled around the common swiveling axis simultaneously with the second X-ray array or solitarily without the second X-ray array by determining:
a first setpoint angle value to the first X-ray array and simultaneously a coupled or a uncoupled second setpoint angle value to the second X-ray array, the coupled second setpoint angle value having a functional relation with the first setpoint angle value and the uncoupled second setpoint angle value not having a functional relation with the first setpoint angle value, or
only the first setpoint angle value to the first X-ray array.

8. A method of operating an X-ray system comprising first and second X-ray arrays, the first X-ray array having a first X-ray source and a first X-ray detector, the second X-ray array having a second X-ray source and a second X-ray detector, the first and second X-ray arrays configured to be swiveled around a common swiveling axis, the method comprising:
swiveling the first X-ray array around the swiveling axis over a first swiveling angle range simultaneously with the second X-ray array or solitarily without the second X-ray array by a control device;
acquiring at specific acquisition angles a plurality of two-dimensional first projections of an examination object only by the first X-ray detector while the first X-ray array is swiveled around the swiveling axis over the first swiveling angle range;
routing the first projections to the control device;
determining a three-dimensional reconstruction of the examination object by the control device exclusively on the basis of the first projections;
using the three-dimensional reconstruction in an examination of the examination object;
removing the second X-ray array from an operating position before the first X-ray array is swiveled around the swiveling axis; and
returning the second X-ray array to the operating position after the first projections have been acquired.

9. A method of operating an X-ray system comprising first and second X-ray arrays, the first X-ray array having a first X-ray source and a first X-ray detector, the second X-ray array having a second X-ray source and a second X-ray detector, the first and second X-ray arrays configured to be swiveled around a common swiveling axis, the method comprising:
swiveling the first X-ray array around the swiveling axis over a first swiveling angle range by a control device;

acquiring at specific acquisition angles a plurality of two-dimensional first projections of an examination object only by the first X-ray detector while the first X-ray array is swiveled around the swiveling axis over the first swiveling angle range;

routing the first projections to the control device;

determining a three-dimensional reconstruction of the examination object by the control device exclusively on the basis of the first projections;

positioning the first and second X-ray arrays;

acquiring a plurality of two-dimensional live projections of the examination object relative to different projection directions by the first and second X-ray arrays after determining the three-dimensional reconstruction;

routing the live projections to the control device; and using the three-dimensional reconstruction and the live projections in an examination of the examination object.

10. The method according to claim 9, wherein first and second X-ray arrays are each positioned according to one of the acquisition angles.

11. The method according to claim 9, further comprising:

determining whether the examination has changed its location based on the live projections by the control device; and updating the three-dimensional reconstruction of the examination object by the control device using the live projections acquired by the first and second X-ray arrays.

12. The method according to claim 11, wherein determining whether the examination object has changed its location includes comparing the live projections to previously recorded two-dimensional projections.

13. The method according to claim 11, further comprising determining two-dimensional reconstruction projections corresponding to the live projections by the control device using the three-dimensional reconstruction of the examination object, wherein determining whether the examination object has changed its location includes comparing the two-dimensional live projections to the two-dimensional reconstruction projections.

14. The method according to claim 11, wherein updating the three-dimensional reconstruction of the examination object relative to at least one of the acquisition angles includes:

acquiring the live projections at the at least one acquisition angle using the first and the second X-ray arrays, updating the corresponding, previously acquired first projections based on the live projections acquired at the at least one acquisition angle, and updating the three-dimensional reconstruction of the examination object by the control device based on the updated first projections.

15. The method according to claim 14, wherein updating the three-dimensional reconstruction of the examination object is further based on the previously acquired first projections.

16. The method according to claim 15, wherein updating the three-dimensional reconstruction of the examination object includes updating precisely one of the first projections using the corresponding live projection acquired by the first or second X-ray array.

17. The method according to claim 15, wherein updating the three-dimensional reconstruction of the examination object includes:

simultaneously swiveling the first and second X-ray arrays over a live swiveling angle range around the swiveling axis, acquiring the live projections by the first and second X-ray arrays at at least two of the acquisition angles, routing to the control device the live projections acquired, at the at least two of the acquisition angles, and updating such first projections corresponding to the live projections acquired at the at least two of the acquisition angles based on the live projections acquired at the at least two of the acquisition angles.

18. The method according to claim 17, wherein the live swiveling angle range is less than half the first swiveling angle range.

19. The operating method according to claim 14, wherein the first and second X-ray detectors are:

arranged opposite the X-ray sources relative to the swiveling axis; and embodied as flat-panel detectors, such that irradiating the object is registered relative to a first irradiation plane using the first X-ray detector and relative to a second irradiation plane using the second X-ray detector.

20. The operating method according to claim 19, wherein such first projections which are updated based on the live projections acquired by the second X-ray array are updated exclusively within the second irradiation plane.

21. The method according to claim 9, further comprising:

selecting a partial volume within the three-dimensional reconstruction of the examination object;

acquiring an area of the examination object corresponding to the partial volume by the first and second X-ray arrays; and updating the three-dimensional reconstruction of the examination object only relative to the partial volume.

22. The method according to claim 9, further comprising:

identifying a location of the examination object into which an instrument has been inserted using the live projections;

reconstructing a two-dimensional representation image from the three-dimensional reconstruction of the examination object; and marking the identified site in the two-dimensional representation image.

23. The method according to claim 9, further comprising:

determining a two-dimensional reconstruction projection corresponding to at least one of the live projections, by the control device; and outputting the at least one live projection in addition to or together with the two-dimensional reconstruction projection.

24. The method according to claim 9, further comprising:

determining a two-dimensional reconstruction projection corresponding to at least one of the live projections, by the control device; and marking in the two-dimensional reconstruction projection such location of the at least one of the two-dimensional live projections at which an instrument is inserted into the examination object.

* * * * *